US008875318B2

(12) United States Patent
Huh (10) Patent No.: US 8,875,318 B2
(45) Date of Patent: Nov. 4, 2014

(54) HEAD BAND (75) Inventor: Moon Young Huh, Seoul (KR)

(73) Assignee: Otos Wing Co., Ltd. (KR)

( * ) Notice: Subject to any disclaimer, the term of this patent is extended or adjusted under 35 U.S.C. 154(b) by 865 days.

(21) Appl. No.: 13/088,623

(22) Filed: Apr. 18, 2011

(65) Prior Publication Data

US 2012/0144565 A1   Jun. 14, 2012

(30) Foreign Application Priority Data

Dec. 13, 2010   (KR) .................. 10-2010-0126858

(51) Int. Cl.
*A42B 7/00* (2006.01)
*A42B 3/14* (2006.01)
*A42B 3/22* (2006.01)
*A61B 19/00* (2006.01)

(52) U.S. Cl.
CPC .................. *A42B 3/145* (2013.01); *A42B 3/225* (2013.01); *A61B 19/5202* (2013.01); *A61B 2019/262* (2013.01)
USPC .................................................. 2/421; 2/416

(58) Field of Classification Search
CPC ............ A42B 3/04; A42B 3/32; A42B 1/242; A42B 1/244; A42B 3/145; A42B 3/225; A41D 13/1161; A41D 2600/202; A61B 19/5202; A61B 2019/262
USPC ................ 2/410, 5, 6.6, 416, 420, 421, 181.6
See application file for complete search history.

(56) References Cited

U.S. PATENT DOCUMENTS

| 2,187,932 | A | * | 1/1940  | Cornell        | 2/8.2   |
|-----------|---|---|---------|----------------|---------|
| 2,194,492 | A | * | 3/1940  | Bowers         | 2/8.1   |
| 2,272,833 | A | * | 2/1942  | Dockson        | 2/8.1   |
| 2,658,200 | A | * | 11/1953 | Bowers, Sr.    | 2/8.1   |
| 2,763,006 | A | * | 9/1956  | Amundsen       | 2/8.1   |
| 3,041,622 | A | * | 7/1962  | Gurtowski      | 2/8.1   |
| 3,047,876 | A | * | 8/1962  | Malcom, Jr.    | 2/9     |
| 3,075,201 | A | * | 1/1963  | Lindblom       | 2/8.1   |
| 4,536,892 | A | * | 8/1985  | Brinkhoff et al. | 2/424 |
| 4,703,879 | A | * | 11/1987 | Kastendieck et al. | 2/422 |
| 4,986,282 | A | * | 1/1991  | Stackhouse et al. | 128/857 |
| 5,077,836 | A | * | 1/1992  | Idoff et al.   | 2/10    |
| 5,412,811 | A | * | 5/1995  | Hildenbrand et al. | 2/10 |
| 5,571,217 | A | * | 11/1996 | Del Bon et al. | 2/9     |
| 5,572,749 | A | * | 11/1996 | Ogden          | 2/421   |
| 5,608,917 | A | * | 3/1997  | Landis et al.  | 2/418   |

(Continued)

FOREIGN PATENT DOCUMENTS

WO    WO 2009048794 A1 *   4/2009

*Primary Examiner* — Alissa L Hoey
(74) *Attorney, Agent, or Firm* — Cantor Colburn LLP (57) ABSTRACT

Disclosed is a head band to assist a user in conveniently wearing head protective equipment on the head. The head band includes a first band part configured to surround the circumference of the head. The first band part includes first sections located at opposite lateral regions of the head and each provided with a coupling piece for coupling with the welding mask, a second section located on a front region of the head, the second section taking the form of an arc-shaped section having a predetermined radius of curvature when unrolled and being adapted to come into close contact at a predetermined gradient with the forehead, and third sections located at a rear region of the head, the third sections being connectable to each other to enable adjustment in the length of the third sections. The first band part comfortably comes into close contact with the forehead, providing wearer comfort.

1 Claim, 11 Drawing Sheets (56) References Cited

U.S. PATENT DOCUMENTS

| | | | |
|---|---|---|---|
| 5,898,949 A * | 5/1999 | Barthold et al. | 2/416 |
| 6,341,382 B1 * | 1/2002 | Ryvin et al. | 2/417 |
| 6,966,074 B2 * | 11/2005 | Huh | 2/414 |
| 7,120,939 B1 * | 10/2006 | Howard et al. | 2/416 |
| 7,222,374 B2 * | 5/2007 | Musal et al. | 2/421 |
| 7,409,723 B2 * | 8/2008 | Huh | 2/8.2 |
| 8,161,576 B2 * | 4/2012 | Lemke et al. | 2/418 |
| 8,201,275 B2 * | 6/2012 | Packard et al. | 2/422 |
| 8,206,327 B2 * | 6/2012 | Wu | 601/46 |
| 8,336,114 B1 * | 12/2012 | Lee | 2/9 |
| 8,370,967 B2 * | 2/2013 | Chen | 2/418 |
| 8,387,162 B2 * | 3/2013 | Huh | 2/8.2 |
| 8,505,121 B2 * | 8/2013 | Ahlgren et al. | 2/417 |
| 8,661,570 B2 * | 3/2014 | Huh | 2/418 |
| 2005/0138719 A1 * | 6/2005 | Huh | 2/416 |
| 2007/0245466 A1 * | 10/2007 | Lilenthal et al. | 2/416 |
| 2007/0245467 A1 * | 10/2007 | Lilenthal et al. | 2/416 |
| 2008/0109947 A1 * | 5/2008 | Dubois | 2/414 |
| 2009/0229041 A1 * | 9/2009 | Tufenkjian | 2/414 |
| 2010/0050325 A1 * | 3/2010 | Wang-Lee | 2/418 |
| 2010/0095438 A1 * | 4/2010 | Moelker | 2/418 |
| 2010/0229274 A1 * | 9/2010 | Ahlgren et al. | 2/8.2 |
| 2010/0229286 A1 * | 9/2010 | Ahlgren et al. | 2/416 |
| 2011/0265254 A1 * | 11/2011 | Ma et al. | 2/420 |
| 2012/0144565 A1 * | 6/2012 | Huh | 2/421 |
| 2012/0311752 A1 * | 12/2012 | Ahlgren et al. | 2/8.2 |

* cited by examiner

HEAD BAND

BACKGROUND OF THE INVENTION

1. Field of the Invention

The present invention relates to a head band usable with head protective equipment, such as a welding mask, a safety helmet, a face shield, etc., to assist a user in conveniently wearing the head protective equipment on the head.

2. Description of the Related Art

Considerable effort and research has been focused on assisting a user, i.e. a wearer, in conveniently wearing head protective equipment, such as a welding shield (welding mask), a safety helmet, a face shield, etc., without encountering any difficulty during welding.

In the case of a welding operation, a welder is likely to encounter several dangers. For example, a strong flash of light may temporarily blind the welder, or a welding material may be scattered toward the welder's face due to sudden heat generated during resistance welding.

A welding mask has been used as a representative example of equipment to protect the welder's eyes and face from the aforementioned dangers. The welding mask contains a head band therein to assist the welder in wearing the welding mask on the head. Both ends of the head band are secured to the welding mask by hinges such that the welding mask may be pivoted upward or downward about the hinges to selectively expose or cover the face.

A conventional head band for use with a welding mask basically includes: a first band part configured to surround the circumference of the head including the forehead and the back of the head; and a second band part extending from one end to the other end of the first band part to surround the crown of the head.

SUMMARY OF THE INVENTION

Therefore, the present invention is directed to obviating a problem of the related art in that the first band part, which is configured to surround the circumference of the head when a wearer wears the conventional head band on the head, cannot comfortably come into close contact with the forehead, causing the wearer inconvenience.

It is another object of the present invention to obviate a problem of the related art in that the first band part, which is configured to surround the circumference of the head when a wearer wears the conventional head band on the head, cannot comfortably come into close contact with the back of the head, causing the wearer inconvenience.

It is a further object of the present invention to obviate a problem of the related art in that only a single second band part is provided to surround the crown of the head when a wearer wears the conventional head band on the head, and the second band part has difficulty conforming to the head of the wearer because adjusting a gradient thereof is difficult, causing the wearer inconvenience.

In accordance with an aspect of the present invention, the above and other objects can be accomplished by the provision of a head band to assist a wearer in wearing a welding mask (welding shield), a face shield, or a safety helmet on the head, the head band including a first band part configured to surround the circumference of the head, wherein the first band part includes a pair of first sections to be located at opposite lateral regions of the head, each first section being provided with a coupling piece for coupling with the welding mask, a second section to be located on a front region of the head, the second section taking the form of an arc-shaped section having a predetermined radius of curvature when completely unrolled and being adapted to come into close contact at a predetermined gradient with the forehead, and a pair of third sections to be located at a rear region of the head, the third sections being connectable to each other so as to enable adjustment in the length of the third sections.

The first section may include a curvilinear bent section extending downward from a rear end of the coupling piece.

The curvilinear bent section may have an angle of 50 degrees to 65 degrees with respect to a horizontal axis of the first section.

A radius of curvature of an imaginary line of the second section extending between horizontal center axes of both the first sections may be in a range of 190 mm to 215 mm.

A central region between the upper and lower ends of the second section may be inwardly convexly raised.

Each third section may be hinged to a distal end of the curvilinear bent section.

The head band may further include a pair of second band parts formed at front ends of the respective first sections, the second band parts being connected to each other in a length adjustable manner to surround a front region of the crown of the head, and a pair of third band parts formed at rear ends of the respective first sections, the third band parts being connected to each other in a length adjustable manner to surround a rear region of the crown of the head.

Each second band part may integrally extend from the corresponding first section to have an angle of 55 degrees to 85 degrees with respect to the horizontal axis of the first section, and each third band part may be hinged to the corresponding first section so as to be rotated by an angle of 55 degrees to 85 degrees with respect to the horizontal axis of the first section.

The third sections may be fitted respectively to left and right ends of a length adjusting lever to enable adjustment in the length of the third sections connected to each other, and a centrally concave cushion member may be coupled to the inner surface of the length adjusting lever so as to come into close contact with the back of the head.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, an exemplary embodiment of the present invention will be described in detail with reference to the accompanying drawings.

The head band of the present invention, as illustrated in FIGS. 1 to 10, includes a first band part 100 configured to surround the circumference of the head. The first band part 100 includes a pair of first sections 110 to be located at opposite lateral regions of the head, each first section 110 being provided with a coupling piece 110a for coupling with, e.g., a welding mask, a second section 120 to be located on a front region of the head, the second section 120 taking the form of an arc-shaped section having a predetermined radius of curvature when completely unrolled and being adapted to come into close contact at a predetermined gradient with the forehead, and a pair of third sections 130 to be located at a rear region of the head, the third sections 130 being connectable to each other so as to enable adjustment in the length of the third sections 130.

Figure 1:
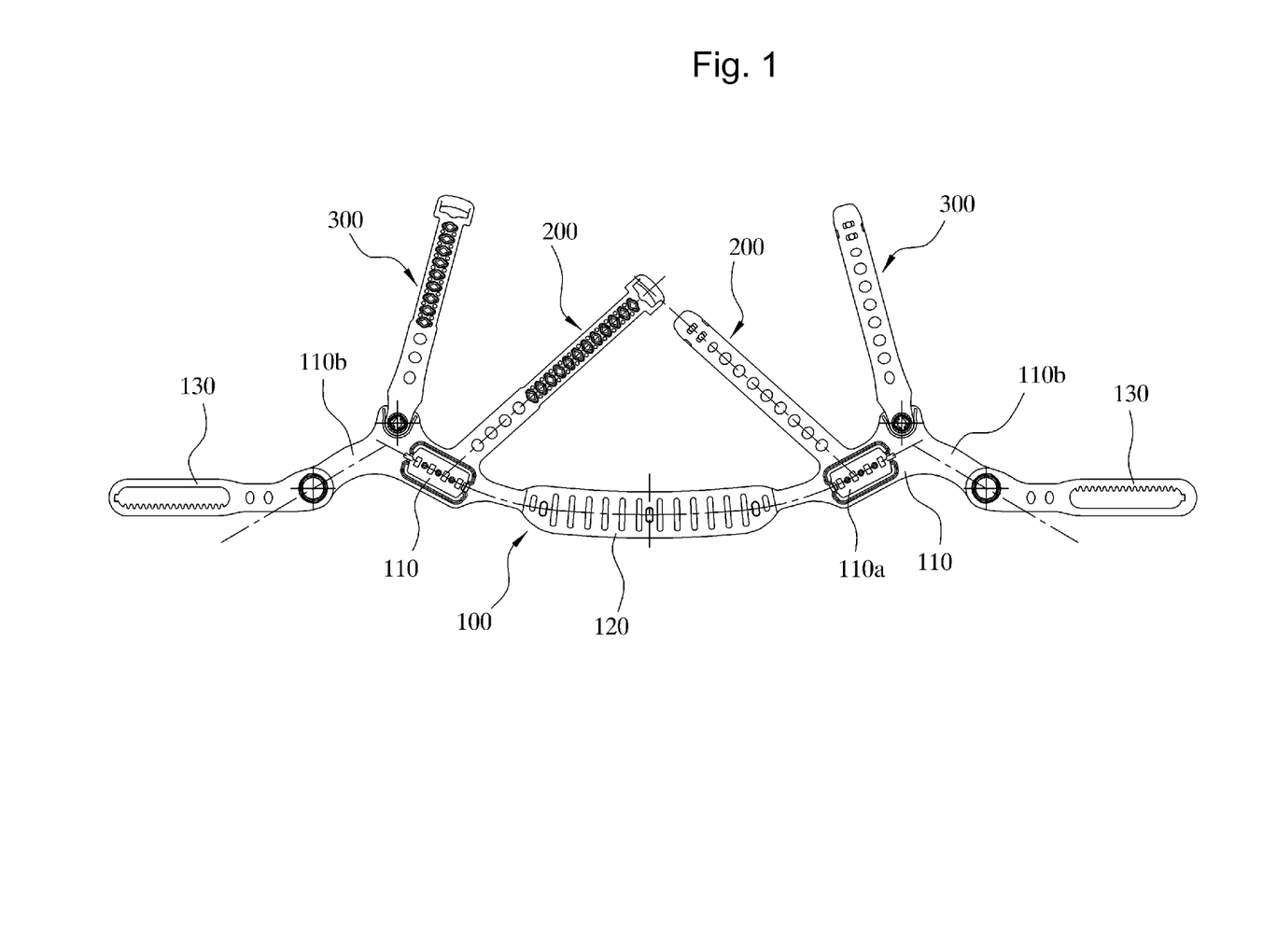
FIG. 1 is a development view illustrating a head band according to the present invention.
Figure 3:
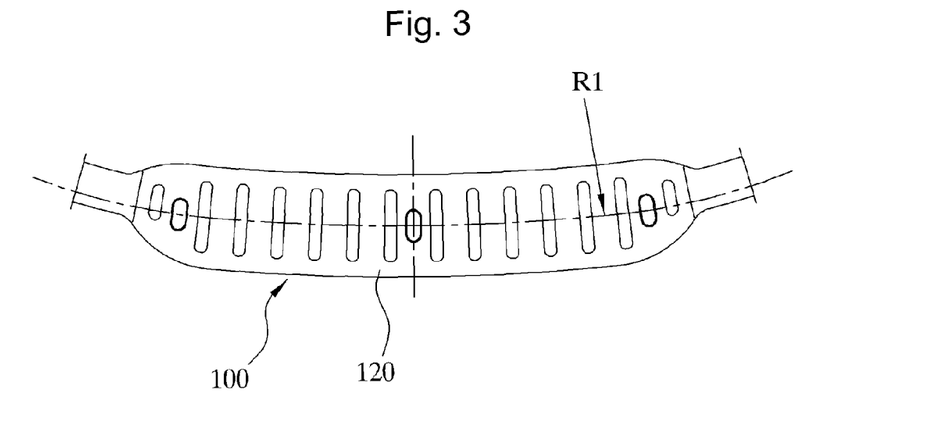
FIG. 3 is an enlarged view illustrating a first section of a first band part of the head band according to the present invention.

More particularly, the present invention has a feature that the second section 120 is configured to come into close contact with the forehead of the wearer. The second section 120 is originally fabricated into an arc-shaped section having a predetermined radius of curvature in an evenly unrolled state thereof as illustrated in FIGS. 1 and 3.

Figure 2:
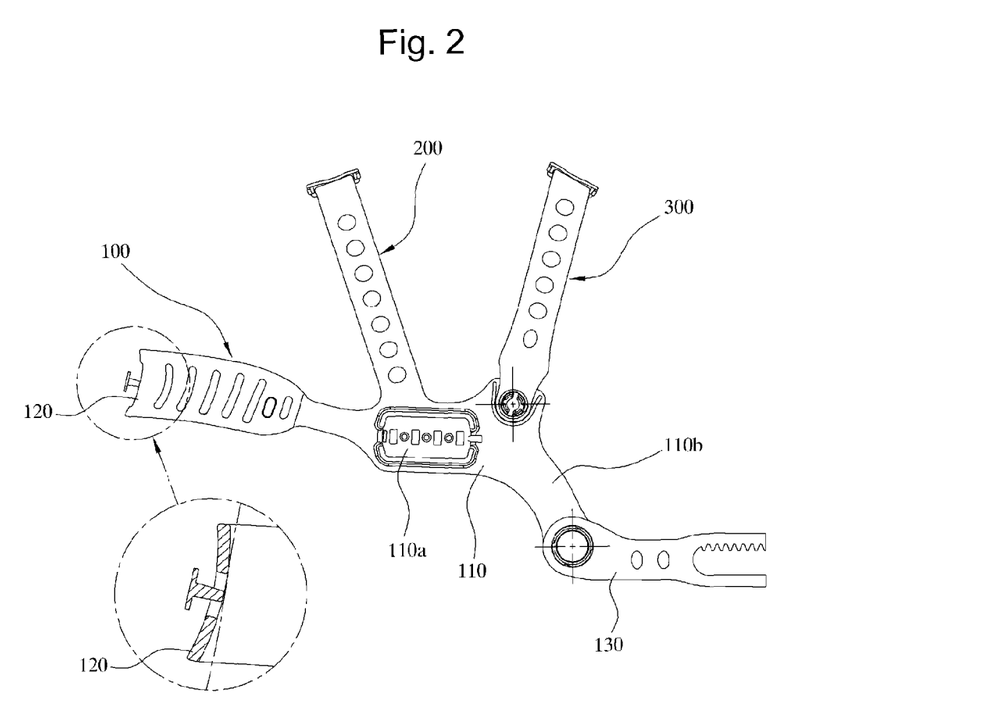
FIG. 2 is a side view illustrating the head band according to the present invention.

However, when the second section 120 is rolled to be worn on the forehead as illustrated in FIG. 2, the second section 120 can be deformed to have a predetermined gradient so as to come into close contact with the forehead.

The coupling piece 110a of the first section 110 serves to couple the head band to the welding mask. Specifically, the coupling piece 110a is hinged to the welding mask to enable pivotal rotation of the welding mask.

The first section 110 includes a curvilinear bent section 110b extending downward from a rear end of the coupling piece 110a. The curvilinear bent section 110b serves to locate the third section 130 at a lower region of the back of the head, thereby allowing the third section 130 to come into close contact with the lower region of the back of the head. This prevents the center of gravity of the welding mask from deviating forward, thereby preventing the head band from easily slipping off in the forward direction.

Figure 4:
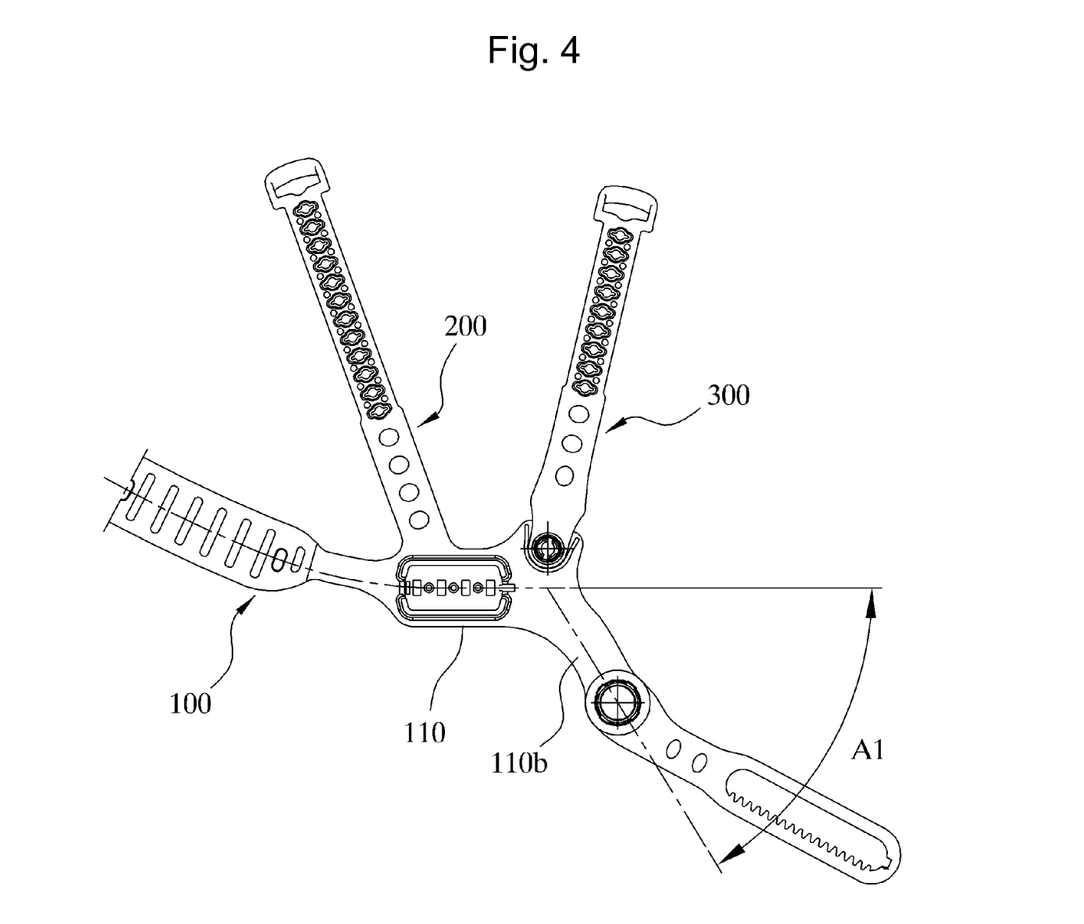
FIG. 4 is a side view explaining a curvilinear bent section included in the first section of the head band according to the present invention.

In the embodiment, as illustrated in FIG. 4, the curvilinear bent section 110b may have an angle A1 of 50 degrees to 65 degrees with respect to a horizontal axis of the first section 110. Most preferably, the angle of the curvilinear bent section 110b is 58 degrees.

The gradient of the second section 120 to ensure that the second section 120 comes into contact with the forehead is adjustable based on the radius of curvature of the arc-shaped second section 120. In the embodiment, as illustrated in FIG. 3, the second section 120 may be configured in such a manner that a radius R1 of curvature of an imaginary line extending between horizontal center axes of both the first sections 110 is in a range of 190 mm to 215 mm. In this case, a straight length of the entire second section 120 in an unrolled state of the second section 120 may be in a range of 250 mm to 290 mm.

Specifically, the second section 120 has a feature that a length L1 of an upper end thereof is always less than a length L2 of a lower end thereof to ensure that the second section 120 comes into close contact with the forehead.

Referring again to FIG. 2, the second section 120 is shaped such that a central region between the upper and lower ends thereof is inwardly convexly raised. This shape may prevent the upper and lower ends of the second section 120 from leaving a mark on the forehead. To this end, the second section 120 is molded to have the inwardly convexly raised central region and thus, the second section 120 maintains the inwardly convexly raised central region even in an unrolled state thereof.

The third sections 130 are adjustable in length to come into close contact with the back of the head. To adjust the length of the third sections 130, the head band of the present invention is provided with a length adjusting lever 400. In the embodiment, as illustrated in FIGS. 7 to 10, the third sections 130 are fitted to left and right ends of the length adjusting lever 400 in a freely length adjustable manner. The length adjusting lever 400 is well known to those skilled in the art and thus, a detailed description thereof will be omitted. The third section 130, as illustrated in FIG. 1, has an elongated hole, upper and lower edges of which are toothed for engagement of the length adjustable lever 400.

A cushion member 410 is coupled to an inner surface of the length adjusting lever 400. The cushion member 410 is centrally concave from upper and lower and left and right sides thereof so as to come into close contact with the back of the head. The centrally concave cushion member 410 comfortably surrounds the back of the head, providing wearer comfort.

In the embodiment, as illustrated in FIGS. 1 and 2, the third section 130 is connected to a distal end of the curvilinear bent section 110b by a hinge. Thus, the third section 130 is pivotally rotatable about the hinge, which allows the third section 130 to more comfortably come into close contact with the back of the head.

The head band of the present invention further includes a pair of second band parts 200 formed at front ends of the respective first sections 110 and a pair of third band parts 300 formed at rear ends of the respective first sections 110. The second band parts 200 are connected to each other in a length adjustable manner to surround a front region of the crown of the head. Similarly, the third band parts 300 are connected to each other in a length adjustable manner to surround a rear region of the crown of the head. Providing the second and third band parts 200 and 300 to surround the front and rear regions of the crown of the head can assist the user in more conveniently wearing the head band.

Figure 5:
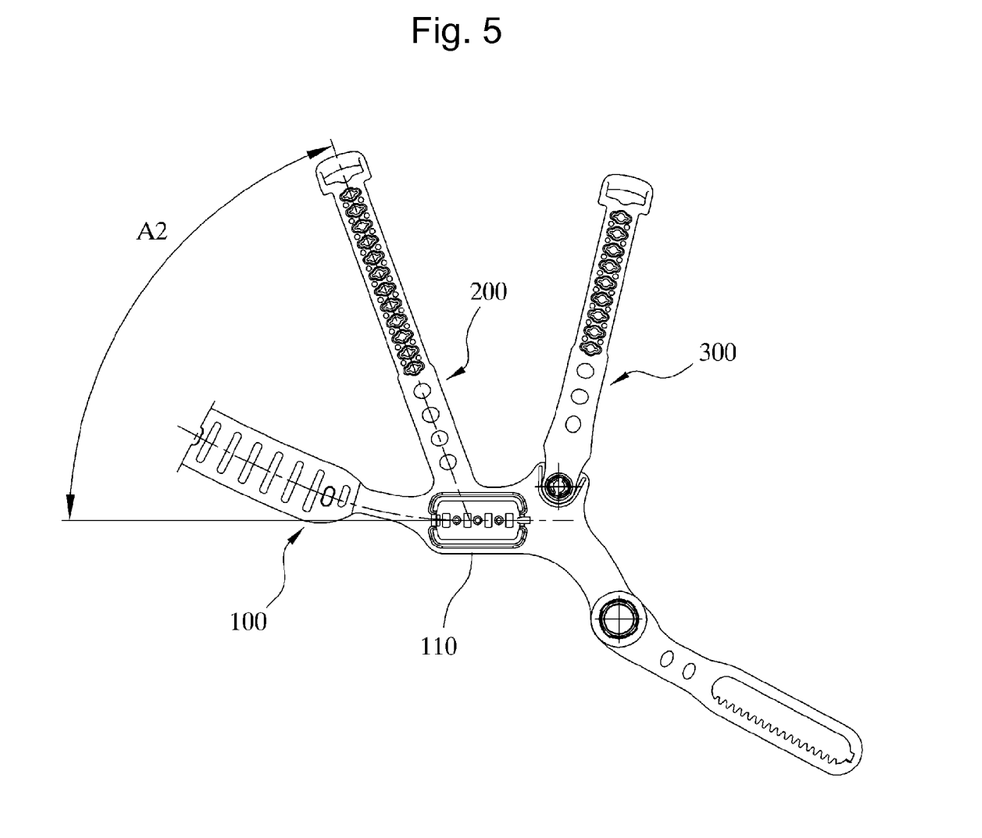
FIG. 5 is a side view illustrating a second band part of the head band according to the present invention.
Figure 6:
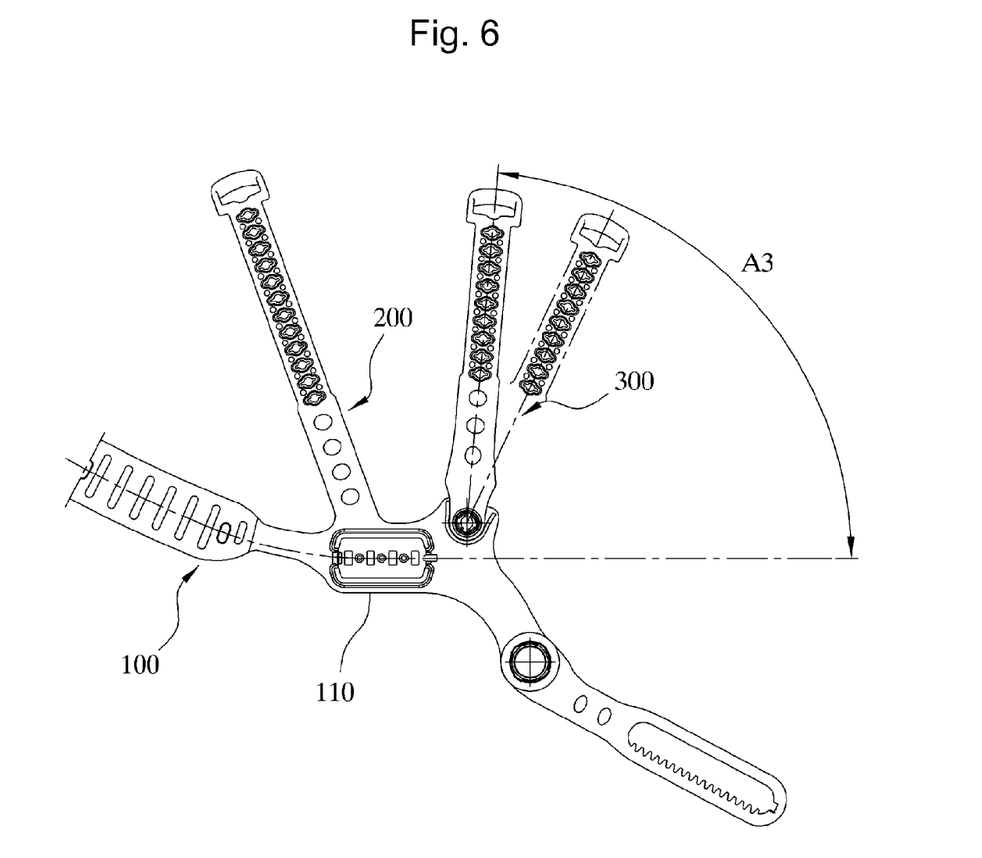
FIG. 6 is a side view illustrating a third band part of the head band according to the present invention.
Figure 7:
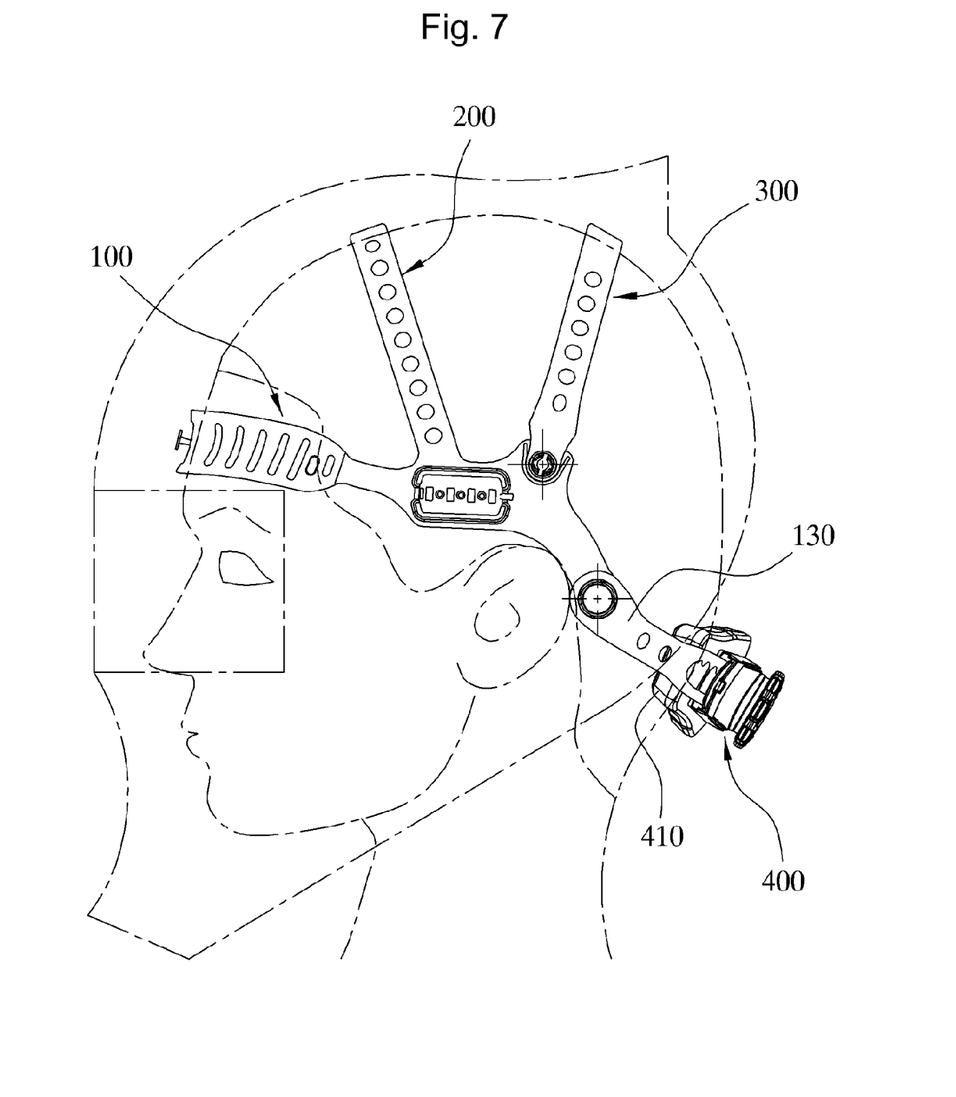
FIG. 7 is a side view illustrating a state in which the head band according to the present invention is worn on the head of a wearer.
Figure 8:
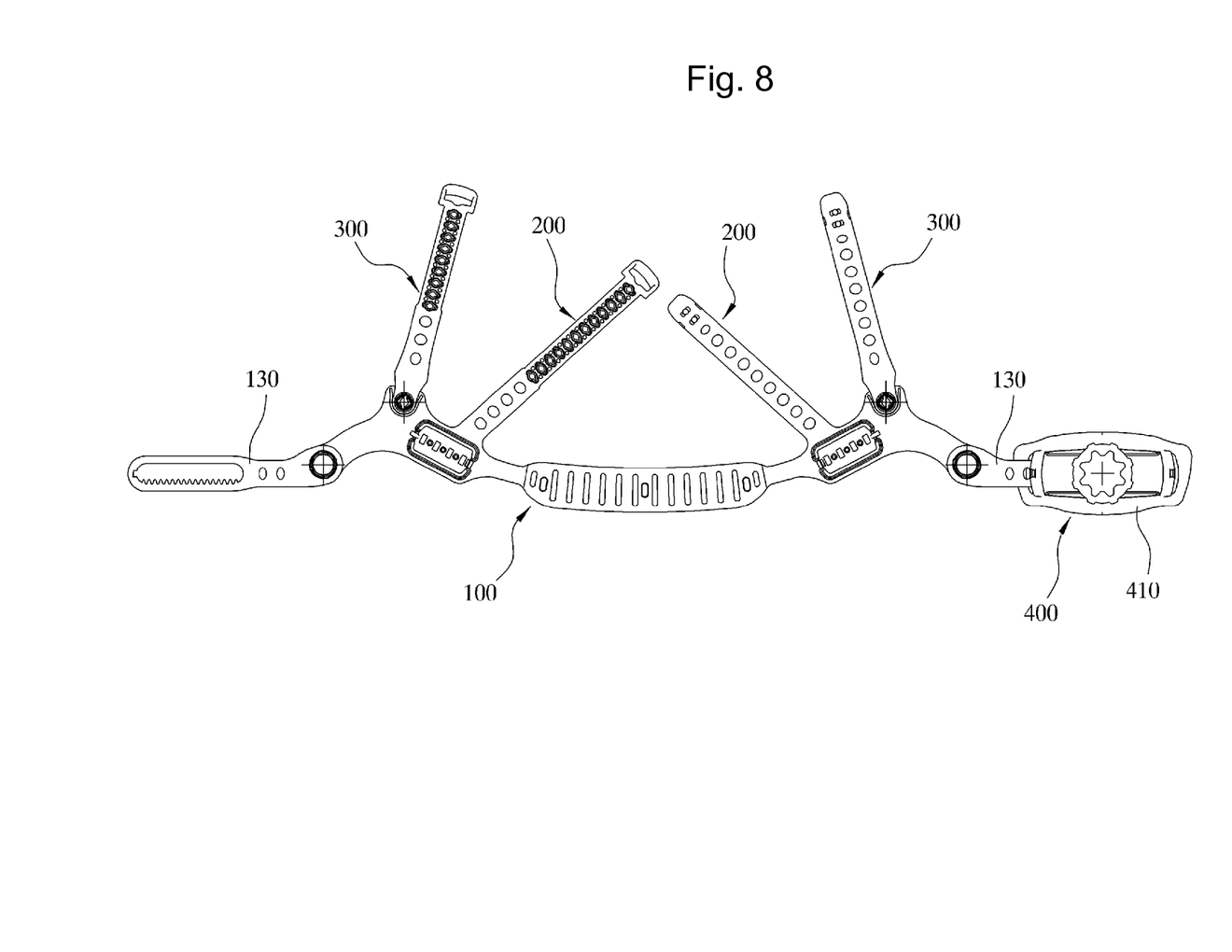
FIG. 8 is a development view explaining a length adjusting lever of the head band according to the present invention.
Figure 9:
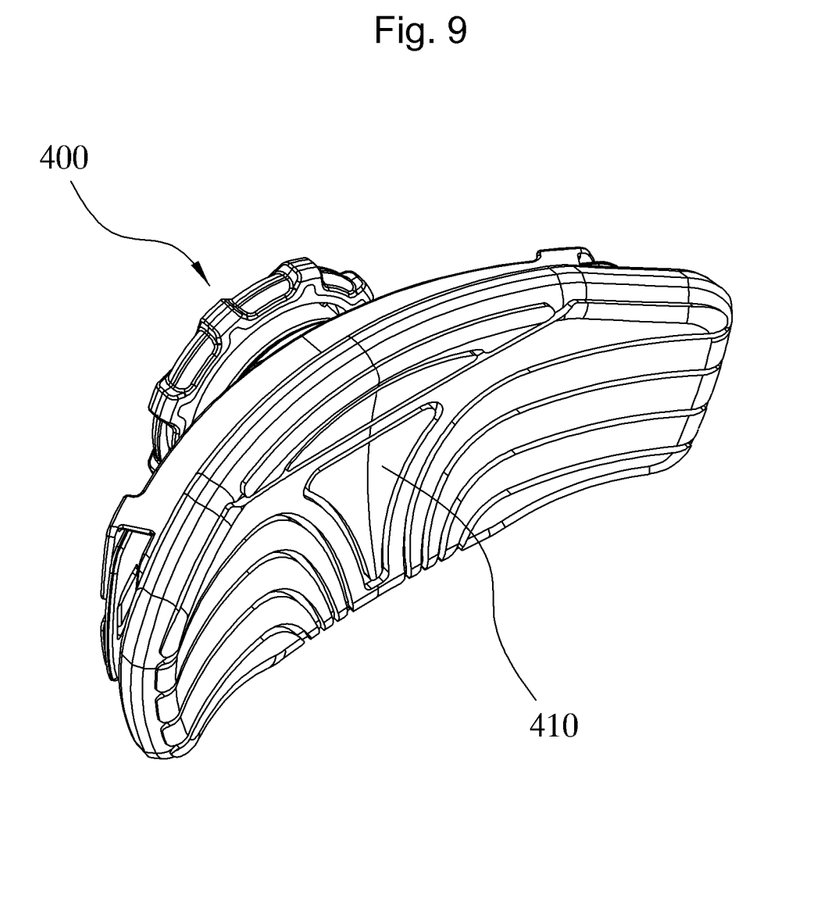
FIG. 9 is a perspective view illustrating the length adjusting lever of the head band according to the present invention.
Figure 10:
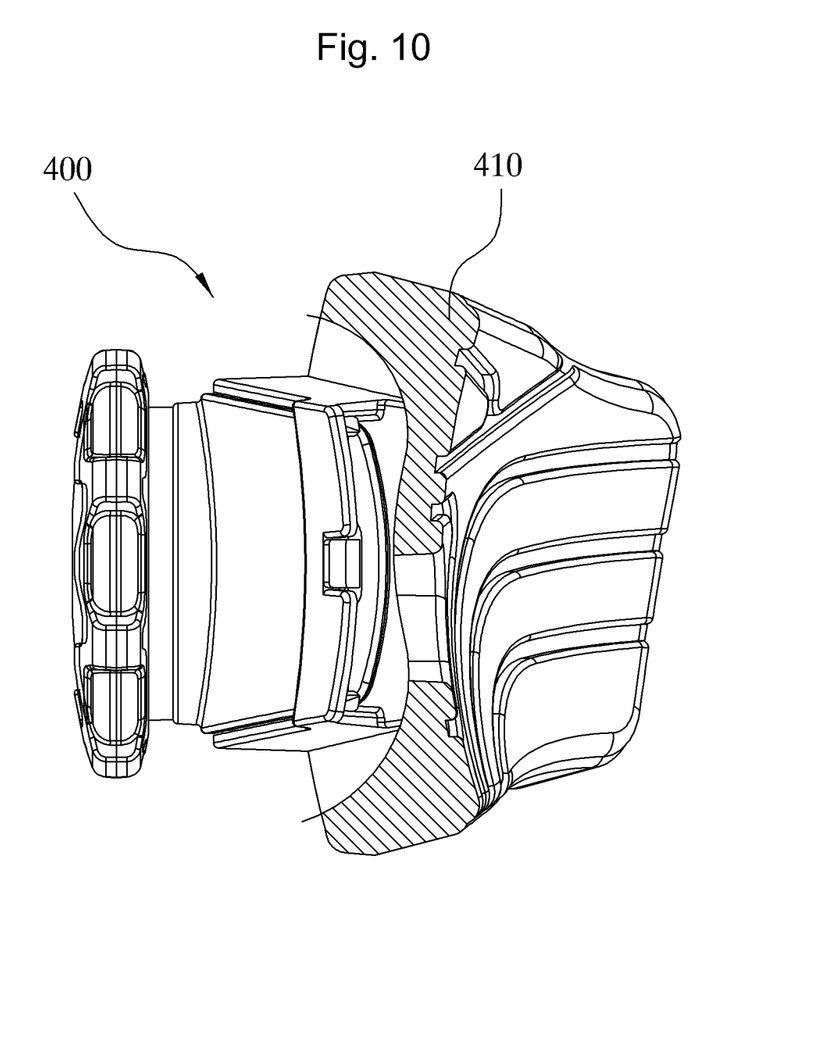
FIG. 10 is a partially sectional view illustrating the length adjusting lever of the head band according to the present invention.

In the embodiment, as illustrated in FIG. 5, the second band part 200 may integrally extend from the first section 110 to have an angle A2 of 55 degrees to 85 degrees with respect to the horizontal axis of the first section 110. Also, in the embodiment, as illustrated in FIG. 6, the third band part 300 may be hinged to the first section 110 so as to be rotated by an angle A3 of 55 degrees to 85 degrees with respect to the horizontal axis of the first section 110.

As illustrated in FIGS. 1 and 2, to allow the second band parts 200 to be connected to each other in a length adjustable manner, one of the second band parts 200 may be provided with a plurality of length adjusting holes and the other second band part 200 may be provided with length adjusting protrusions to be inserted into selected ones of the length adjusting holes. This length adjusting configuration is equally applied to the third band parts 300.

With the above described configuration, owing to the fact that the first band part 100 to surround the circumference of the head comfortably comes into close contact with the forehead and the back of the head, the head band of the present invention can provide the wearer with enhanced convenience.

In addition, as a result of providing the second band parts 200 and the third band parts 300 to surround both the front and rear regions of the crown of the head and in particular, providing the third band parts 300 with a convenient angle adjustment function, more convenient wearing of the head band can be accomplished.

Figure 11:
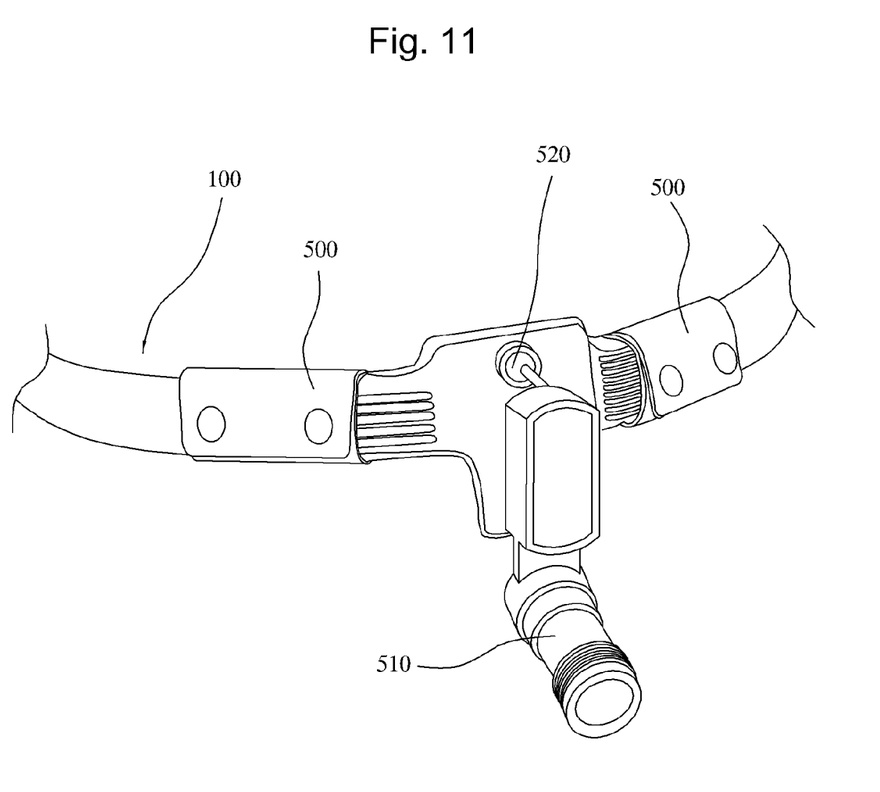
FIGS. 11 and 12 are views illustrating use of a head hand, to which a medical light is mounted.
Figure 12:
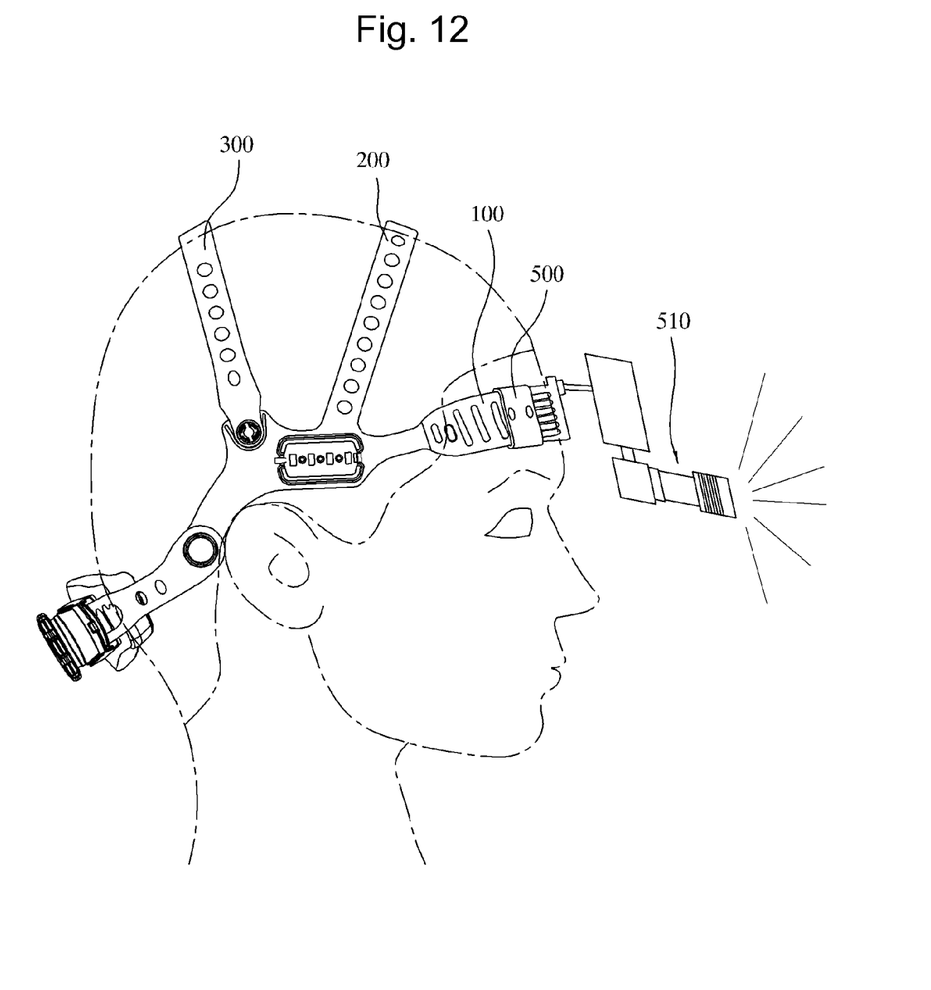

FIGS. 11 and 12 are views illustrating use of a head hand, to which a medical light is mounted.

The first band part 100 of the head band, which comfortably comes into close contact with the forehead, exhibits sufficient rigidity to support the weight of a light 510. Moreover, the second band parts 200 and the third band parts 300, which surround both the front and rear regions of the crown of the head, serve to distribute load of the light 510, which allows the first band part 100 to more firmly support the light 500.

A pair of fastening bands 500 may be coupled to opposite ends of the first band part 100 to firmly secure the light 510. In addition, a connector 520 may be interposed between the first band part 110 and the light 510 to ensure easy direction change of the light 510.

It will be appreciated that the head band having the above described configuration may be applied to a welding mask (welding shield), a face shield, a safety cap or helmet, and a medical light fixture within the scope of the invention.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A head band to assist a wearer in wearing a welding mask (welding shield), a face shield, or a safety helmet on the head, the head band comprising:
    a first band part configured to surround the circumference of the head;
    a pair of second band parts formed at front ends of the respective first sections, the second band parts being connected to each other in a length adjustable manner to surround a front region of the crown of the head: and
    a pair of third band parts formed at rear ends of the respective first sections, the third band parts being connected to each other in a length adjustable manner to surround a rear region of the crown of the head,
    wherein the first band part includes a pair of first sections to be located at opposite lateral regions of the head, each first section being provided with a coupling piece for coupling with the welding mask, a second section to be located on a front region of the head, the second section taking the form of an arc-shaped section having a predetermined radius of curvature when completely unrolled and being adapted to come into close contact at a predetermined gradient with the forehead, and a pair of third sections to be located at a rear region of the head, the third sections being connectable to each other so as to enable adjustment in the length of the third sections,
    wherein a radius of curvature of an imaginary center line of the second section extending between horizontal center axes of both the first sections is in a range of 190 mm to 215 mm,
    wherein a length of an upper end of the second section is less than a length of a lower end of the second section to allow the second section to come into close contact with the forehead,
    wherein a central region between the upper and lower ends of the second section is inwardly convexly raised in order to prevent the upper and lower ends of the second section from leaving a mark on the forehead,
    wherein the third sections are fitted respectively to left and right ends of a length adjusting lever to enable adjustment in the length of the third sections connected to each other, and a cushion member, which is centrally concave from upper and lower sides and from left and right sides thereof, is coupled to the inner surface of the length adjusting lever so as to come into close contact with the back of the head,
    wherein each second band part integrally extends from the corresponding first section to have a fixed angle between 55 degrees to 85 degrees with respect to the horizontal axis of the first section, and each third band part is hinged to the corresponding first section so as to be rotated by an angle of 55 degrees to 85 degrees with respect to the horizontal axis of the first section such that only one pair of the pair of second band parts and the pair of third band parts is rotated with respect to the horizontal axis of the first section.

* * * * *